United States Patent [19]

Potaczek

[11] 4,356,819
[45] Nov. 2, 1982

[54] ARTICLE OF MANUFACTURE HAVING ADHESIVE PROPERTIES

[75] Inventor: Jan J. Potaczek, Leicester, England

[73] Assignee: Advance Tapes (U.K) Limited, Leicester, England

[21] Appl. No.: 132,071

[22] Filed: Mar. 20, 1980

[30] Foreign Application Priority Data

Mar. 21, 1979 [GB] United Kingdom ............... 7909956

[51] Int. Cl.³ ..................... A61F 5/44; A61L 15/06
[52] U.S. Cl. ................... 128/156; 128/283; 524/22; 524/24; 524/55; 524/517; 525/194; 525/207; 523/111
[58] Field of Search ............... 106/208, 135, 137, 209; 260/8, 17.4 ST, 117; 128/156, 283; 525/194, 207; 536/114; 524/22, 24, 55, 517; 523/111

[56] References Cited

U.S. PATENT DOCUMENTS

| | | | |
|---|---|---|---|
| 2,866,772 | 12/1958 | Sellers | 260/45.5 |
| 2,997,464 | 8/1961 | Sellers | 260/78.5 |
| 3,245,933 | 4/1966 | Muskat | 260/29.6 |
| 3,339,546 | 9/1967 | Chen | 128/156 |
| 3,640,741 | 2/1972 | Etes | 106/170 |
| 3,805,789 | 4/1974 | Marson | 128/283 |
| 3,878,151 | 4/1975 | Dachs | 260/29.6 T |
| 3,906,951 | 9/1975 | Ling | 128/283 |
| 3,908,658 | 9/1975 | Marson | 128/283 |
| 3,980,084 | 8/1976 | Kross | 128/283 |

FOREIGN PATENT DOCUMENTS

| | | |
|---|---|---|
| 2441626 | 3/1975 | Fed. Rep. of Germany . |
| 2277597 | 2/1976 | France . |
| 2393566 | 1/1978 | France . |
| 2392076 | 12/1978 | France . |
| 2396542 | 2/1979 | France . |
| 1307968 | 2/1973 | United Kingdom . |

OTHER PUBLICATIONS

Chem. Abs. vol. 81, 1974, 65513m.
Whistler "Industrial Gums" 1973, p. 248.

*Primary Examiner*—Allan Lieberman
*Assistant Examiner*—Pat Short
*Attorney, Agent, or Firm*—W. R. Hulbert

[57] ABSTRACT

An article of manufacture with adhesive properties comprising a gelatinous adhesive composition dispersed in a plastics matrix. The gelatinous adhesive composition is the resulting product of heating together in the absence of solvent at least one polyhydric alcohol and at least one material selected from the group consisting of gelatin, naturally occurring high molecular weight polysaccharide gums, and resins which are a copolymer of a vinyl ether and a second component selected from organic acid anhydrides and their corresponding free acids. Heating promotes a chemical reaction between the components and also drives off water produced in the reaction which is carried substantially to completion.

17 Claims, No Drawings

ARTICLE OF MANUFACTURE HAVING ADHESIVE PROPERTIES

DESCRIPTION

This invention relates to articles of manufacture having adhesive properties, and useful, for example, as protective plasters or dressings or as rings, washers or the like in surgical appliances such as ostomy appliances.

Conventional pressure-sensitive plasters comprise an adhesive based on a rubber/resin mixture. Such plasters adhere with difficulty to moist body surfaces and, even then, under movement of the body they may easily detach from the skin. There is a particular need for improved protective plasters which may be used in the management of colostomies and ileostomies and similar surgical operations. The ostomy appliances provided for patients who have had such an operation have generally included a sealing ring supposedly for preventing draining waste material which commonly includes active gastric juices from coming into contact with the patient's skin surrounding the stoma, and thereby attacking the skin, or from leaking thereby producing embarrasing odour and soiling of the patient's clothing. Such ostomy sealing rings have not always proved reliable and additional sealing compositions in paste form which may be squeezed from a toothpaste-like tube have been suggested to overcome this problem but have not found wide application, being difficult for the patient himself to use.

In one aspect of the present invention, we provide an article or manufacture, having adhesive properties, and comprising a plastics matrix in which is dispersed a gelatinous adhesive composition comprising the product resulting from heating together:

(a) one or more polyhydric alcohols, and
(b) gelatin, and/or a naturally occurring high molecular weight polysaccharide gum, and/or a resin which is a copolymer of a vinyl ether and an organic acid anhydride and/or its corresponding free acid, to promote chemical reaction between components (a) and (b).

The chemical reaction which occurs on heating between the said components (a) and (b) is essentially the formation of an ester.

We believe many of the said adhesive compositions to be novel, and certain of the said novel adhesive compositions comprise one aspect of our co-pending Patent Application Ser. No. 131,891 ("Gelatinous Articles and Compositions"), filed Mar. 20, 1981, which claims priority from our earlier British Patent Application No. 7909967, to which reference may also be made.

The gelatinous adhesive compositions described herein may be regarded as means relating to an essential element of the present invention for putting that invention into effect.

The preferred polysaccharide gum is Karaya, a natural substance occurring in the bark of certain trees and which appears to be a high molecular weight polysaccharide formed by the condensation of certain unhydro-monosaccharide units, of which those derived from D-gelacturonic acid, D-galactose and L-rhammose are the most important. Other naturally occurring high molecular weight polysaccharide gums which we have found to be useful include gum Tragacanth and gum Arabic.

The preferred resin is a methyl vinyl ether/maleic anhydride copolymer of which a range of suitable resins is available under the trade name Gantrez from Gaf (GB) Limited and under the trade name Viscofas from Imperial Chemical Industries Ltd. We prefer to use Gantrez AN139, or Viscofas L.30.

Suitable polyhydric alcohols include but are not limited to glycerol, sorbitol, pentaerythritol and polyvinylalcohol.

Our gelatinous adhesive compositions have inherent tack and water swelling (absorbing) purposes. The resultant article of manufacture in which the adhesive composition is dispersed in a suitable plastics matrix must retain these properties. Any of the conventional film forming elastic binder plastics materials which are compatible with skin tissue may be employed, though we have found that best results are obtained when at least the major part of the plastics matrix material comprises one or more copolymers of ethylene and vinyl acetate. A range of such copolymers is available from Bayer AG. under the trade name Levapren. We have obtained good results by employing a blend of a high molecular weight such copolymer, Levapren L452, and a low molecular weight such copolymer, Levapren KH8160. Other film forming plastics such as polyisobutylene may optionally be added to the blend or substituted.

The gelatinous adhesive composition can be made either in a heated reaction vessel or preferably in situ during blending with the other ingredients forming the article in a heated Z-blade mixer, the blend being subsequently allowed to solidify, suitably in a mould.

The specific gel content of the gelatinous adhesive composition may readily be adjusted to obtain a desired degree of water swelling (absorbing) capability. The gel structure may be altered by varying the proportions of the reacting ingredients and by employing a crosslinking resin such as glyoxal or citric acid. Melamine resin is also an effective crosslinking agent for the composition but may sensitise the skin of some people and is therefore less preferred.

Our gelatinous adhesive compositions have very useful inherent pressure-sensitive properties, enabling them to act as the sole or main tackifying agent in adhesive articles in accordance with this invention, such as protective plasters or dressings, or rings, washers, or the like, in surgical appliances such as ostomy appliances. The resultant articles adhere readily to dry or moist human body surfaces.

The physical characteristics of the adhesive articles, such as tack, plasticity, cohesive strength and moisture absorbency, may be modified by admixing other substances such as: viscosity modifiers, e.g. micronised silica; tack modifiers, e.g. polyvinylpyrrolidone resin (which in glycerol forms a tacky viscous compound); fillers e.g. calcium carbonate; crosslinking agents, e.g. glyoxal or citric acid; antimicrobial agents; and plasticisers, e.g. paraffin oil. Selection of the polyhydric alcohol may also be used to adjust the physical properties of the articles. Thus when the polyhydric alcohol is glycerol the article has substantial water absorbing properties, and may eventually swell unduly or even begin to dissolve; substitution of glycerol wholly or partially by sorbitol may avoid this. Pentaerythritol is not soluble to any great extent. The presence of polyvinylalcohol enhances adhesion to the skin.

We have found that particularly satisfactory ostomy plasters result when the gelatinous adhesive composition is present in an amount from 30 to 55 percent by weight.

The most satisfactory blends for forming ostomy plasters are those comprising 40 to 50 percent by weight of an adhesive composition resulting from the chemical reaction between sorbitol and/or glycerol and Karaya gum. The ostomy plasters we have made from this glend are soft and pliable, have good adhering qualities to dry and moist skin, are resistant to plastic flow at body temperature and, owing to the Karaya gum content, also possess skin healing properties.

When an adhesive article in accordance with this invention is embodied as a protective plaster or dressing, it preferably has a backing sheet to prevent the tacky plaster or dressing from sticking to clothing etc. A thin, suitably water impermeable, plastics film, for example of polyethylene may be employed. The film is suitably provided with perforations which assist in getting rid of occluded air bubbles during the lamination process. The plasters may be formed as a sheet which may be cut into desired shapes and sizes in a subsequent operation.

The following examples will illustrate the invention:

EXAMPLE 1

300 grams of high molecular weight ethylene/vinyl acetate copolymer, manufactured under the trade name Levapren L452, and 100 grams of low molecular weight ethylene/vinyl acetate copolymer, manufactured under the trade name Levapren KH 8160, were placed in a Z-blade mixer heated at 80°–90° and mixed until a uniform dough was obtained. Then 85 grams of glycerine, 80 grams of Karaya gum and 2 grams of Nipastat (a mixture of p-hydro-benzoic acid esters produced by Nipa Laboratories Limited and having anti-microbial properties) were added and mixed for one hour at 80°–90° C., when at the end of this period a uniform dispersion of the gelatinous adhesive composition was obtained in the plastics matrix. Part of the dispersion was pressed to a thin sheet in an hydraulic press maintained at 130° C. The thus formed adhesive sheet was laminated to a perforated thin polyethylene film and then cut into plasters of desired shapes and sizes. The remainder of the dispersion was moulded to produce a solid mass.

EXAMPLE 2

The procedure of Example 1 was repeated but with the quantity of Nipastat reduced to 1 gram. Comparison of the products of the two examples showed that the reduced Nipastat content products were less likely to sensitise skin.

EXAMPLE 3

300 grams of Levapren L452 and 300 grams of Levapren KH 8160 were placed in a Z-blade mixer heated at 80°–90° C. and mixed until a uniform dough was obtained. Then 450 grams of glycerine, 60 grams of Kollidon 90 (polyvinyl pyrrolidone resin manufactured by BASF Limited), 150 grams of Gantrez AN 139 (methyl vinyl ether/maleic anhydride copolymer resin sold by Gaf (GB) Limited) and 2 grams of Nipastat were added and mixed for one hour at 80°–90° C. Part of the dispersion was pressed to a thin sheet in an hydraulic press maintained at 130° C., and the resultant adhesive sheet laminated to a perforated thin polythene film. Satisfactory ostomy plasters were obtained.

EXAMPLE 4

The procedure of Example 3 was repeated but with the Nipastat content reduced to 1 gram. Comparison of the resulting ostomy plasters showed that those of Example 4 exhibited less likelihood of sensitising skin as compared with those of Example 3.

EXAMPLE 5

The process of Example 1 was followed except that 20 grams of the Karaya gum was replaced by 20 grams of Gantrez AN 139.

EXAMPLE 6

200 grams of Levapren 452 and 200 grams of polyisobutylene (Vistanex LM-MH manufactured by Esso Co. Ltd) were blended in a Z-blade mixer at 90° C. Then were added: 2 grams of Nipastat, 100 grams of micronised amorphous silica (Syloid 244 manufactured by Grace GmbH), 50 grams of Kollidon 90, and 110 grams of Karaya gum. The blend was mixed to obtain uniform dispersion. Next 150 grams of glycerol and 100 grams of paraffin were added, followed by mixing, still maintaining a temperature of 90° C., for one hour. The further stages were as per Example 1.

EXAMPLE 7

Example 6 was repeated with 1 gram only of Nipastat and the results compared. The reduced Nipastat content plasters of Example 7 were found less likely to sensitise skin.

EXAMPLE 8

1500 grams of Vistanex LM-MH and 500 grams of Levapren 452 were placed in a Z-blade mixer heated at 90°–100° C. and mixed until a uniform plastics dough was obtained. Then 900 grams of Karaya gum, 600 grams of glycerol, 400 grams of sorbitol and 2 grams of Nipastat were added and mixed for one hour at 90°–100° C., when at the end of this time a uniform dispersion of the hydrocolloid gelatinous adhesive composition in the plastics matrix was obtained. Part of the dispersion was pressed to a thin sheet in a hydraulic press maintained at 120° C. The resulting adhesive sheet was laminated to perforated thin polyethylene film and then converted into plasters of desired shapes and sizes. Satisfactory ostomy plasters were obtained.

EXAMPLE 9

200 grams of sorbitol and 200 grams of Karaya gum were placed in a glass container and heated at 120° C. in an oven for one hour, stirring the contents every 15 minutes. After cooling to room temperature, a brittle mass resulted. Test showed that this mass was a gelatinous hydrocolloid adhesive composition. It was found to swell and eventually break up into gel particles in water at ambient temperature, but it did not completely dissolve.

200 grams of the sorbitol/Karaya gum hydrocolloid adhesive composition was blended with 150 grams of Vistanex LM-MH and 50 grams of Levapren 452 and moulded in an open dished mould at 120° C. to produce an ostomy sealing ring.

EXAMPLE 10

The procedure of Example 9 was repeated first with 200 grams of pentaerythritol and second with 200 grams of polyvinylalcohol substituted for the sorbitol and the results compared. The ostomy sealing rings formed using pentaerythritol tended to remain relatively hard and not greatly to swell absorbing moisture when in contact with the skin and are therefore in our view less preferable. The rings formed with polyvinylalcohol exhibited particularly good adhesion to skin.

The above Examples all involve production of the gelatinous adhesive compositions in situ in the plastics matrix. We shall now describe below further Examples in which production of the gelatinous adhesive composition is performed as a first step.

EXAMPLE 11

40 grams of glycerine and 30 grams of gelatin were placed in a glass jar and heated at 110° C. in an oven for 2 hours, stirring the contents every 15 minutes. At the end of the curing cycle a thick viscous mass resulted. Part of this glycerine/gelatin adhesive composition was blended with about the same weight of a mixture of equal parts of Levapren L452 and Levapren KH 8160 and moulded in an open dished mould at 120° C. to produce an ostomy sealing ring or washer.

EXAMPLE 12

The process of Example 11 was followed except that instead of 30 grams of gelatin 35 grams of gum Tragacanth was used.

EXAMPLE 13

The procedure of Example 11 was followed except that instead of 30 grams of gelatin, there was substituted a mixture of 27 grams of gum acacia and 2 grams of Madurit 5458 (a melamine resin manufactured by Hoechst of Germany).

EXAMPLE 14

The procedure of Example 13 was repeated first with 2 grams of citric acid substituted for the Madurit 5458 and second with 2 grams of glyoxal obtained from BDH Chemicals Ltd. substituted for the Madurit 5458. The products resulting were found superior in each case to those of Example 13 in being less likely to induce sensitivity in skin.

Pressure-sensitive plasters produced in accordance with this invention are useful in the management of colostomies and ileostomies. We have found that the specific plasters described adhere firmly and for extended period of time to moist human body surfaces. Unlike conventional pressure-sensitive plasters comprising an adhesive based on rubber-resin mixture, our plasters will adhere firmly over long periods of time. They are soft and pliable, conform to the contours of the body surface and do not peel or detach even from moist skin during the normal activities of the person wearing them. Indeed moisture seems to assist adhesion.

Articles having inherent pressure-sensitive characteristics can readily be moulded in a variety of shapes and configurations by following our techniques. The specific examples given are not intended to be limiting.

Protective plasters and dressings and ostomy rings and washers produced in accordance with the present invention possess one notable advantage as compared with those ostomy rings, washers, and plasters of which we are aware and which are on general use in the United Kingdom at the date of this Application: namely, our plasters, dressings, rings and washers are markedly less liable to $\gamma$-radiation embrittlement or softening and so can readily be sterilized by subjection to $\gamma$-radiation.

When rings or washers in accordance with this invention are to be used in ostomy appliances, a base such as aluminium hydroxide may be added to the blend prior to moulding to neutralize acid present in the drainage into the appliance.

What I claim is:

1. An article of manufacture, having adhesive properties, and comprising a plastics matrix in which is dispersed a gelatinous adhesive composition present in quantities between about 30% and 50% by weight of the dispersion, said gelatinous adhesive composition comprising the product resulting from heating together in the absence of solvent:
   (a) at least one polyhydric alcohol, and
   (b) at least one material selected from the group consisting of gelatin, naturally occurring high molecular weight polysaccharide gums, and resins which are a copolymer of a vinyl ether and a second component selected from organic acid anhydrides and their corresponding free acids, to promote chemical reaction between components (a) and (b) and to drive off water produced in the reaction, the reaction being carried substantially to completion.

2. An article according to claim 1, wherein the naturally occurring high molecular weight polysaccharide gums are selected from the group consisting of gum Karaya, gum Tragacanth, and gum Arabic (gum Acacia).

3. An article according to claim 1, wherein the polyhydric alcohol is selected from the group consisting of glycerol, sorbitol, pentaerythritol and polyvinylalcohol.

4. An article according to claim 1, wherein the said copolymer resin comprises a copolymer of a methyl vinyl ether and a second component selected from maleic anhydride and its free acid.

5. An article according to claim 1, wherein the physical characteristics of the said article including tack, plasticity, cohesive strength and moisture absorbency are modified by the incorporation into said article of one or more materials selected from viscosity modifiers, tack modifiers, fillers, crosslinking agents, antimocrobial agents, and plasticisers.

6. An article according to claim 5, wherein micronised silica is present as a viscosity modifier.

7. An article according to claim 5, wherein polyvinylpyrrolidone resin is present as a tack modifier.

8. An article according to claim 5, wherein the crosslinking agent is selected from glyoxal, citric acid, and melamine resin.

9. An article according to claim 5, wherein paraffin oil is present as a plasticiser.

10. An article according to claim 1, wherein the gelatinous adhesive composition is formed in situ in the plastics matrix.

11. An article according to claim 1, wherein the plastics matrix material is selected from elastic binder plastics materials which are compatible with skin tissues.

12. An article according to claim 11, wherein at least the major part of the plastics matrix material comprises at least one copolymer of ethylene and vinyl acetate.

13. An article according to claim 11, wherein the plastics matrix material includes polyisobutylene.

14. An article according to claim 1, when moulded to form a component of a surgical appliance or the like.

15. An article of manufacture according to claim 1, moulded to form an ostomy ring or washer.

16. A plaster or protective dressing consisting of an article of manufacture according to claim 1 which has been pressed to a thin adhesive sheet in an hydraulic press and then cut into required shapes.

17. A plaster or protective dressing according to claim 16, provided with a backing sheet in the form of a thin water impermeable plastics film, for example of polyethylene.

* * * * *